US011890264B2

(12) United States Patent
Gross et al.

(10) Patent No.: US 11,890,264 B2
(45) Date of Patent: *Feb. 6, 2024

(54) MIGRAINE PREVENTION AND TREATMENT

(71) Applicant: UNIVERSITATS-KINDERSPITAL BEIDER BASEL, Basel (CH)

(72) Inventors: Elena Gross, Basel (CH); Dirk Fischer, Allschwil (CH)

(73) Assignee: UNIVERSITATS-KINDERSPITAL BEIDER BASEL, Basel (CH)

(*) Notice: Subject to any disclaimer, the term of this patent is extended or adjusted under 35 U.S.C. 154(b) by 201 days.

This patent is subject to a terminal disclaimer.

(21) Appl. No.: 17/335,319

(22) Filed: Jun. 1, 2021

(65) Prior Publication Data
US 2021/0338618 A1 Nov. 4, 2021

Related U.S. Application Data

(63) Continuation of application No. 16/472,309, filed as application No. PCT/EP2017/083880 on Dec. 20, 2017, now Pat. No. 11,166,928.

(30) Foreign Application Priority Data

Dec. 21, 2016 (EP) ..................... 16206018
Feb. 1, 2017 (EP) ..................... 17154258

(51) Int. Cl.
A61K 31/194 (2006.01)
A61P 25/06 (2006.01)
A61K 9/00 (2006.01)
A61K 31/19 (2006.01)
A61K 31/191 (2006.01)
A61K 31/197 (2006.01)
A61K 31/198 (2006.01)
A61K 31/405 (2006.01)

(52) U.S. Cl.
CPC .......... A61K 31/194 (2013.01); A61K 9/0053 (2013.01); A61K 31/19 (2013.01); A61K 31/191 (2013.01); A61K 31/197 (2013.01); A61K 31/198 (2013.01); A61K 31/405 (2013.01); A61P 25/06 (2018.01)

(58) Field of Classification Search
CPC .................................................. A61K 31/194
See application file for complete search history.

(56) References Cited

U.S. PATENT DOCUMENTS

| 5,420,335 | A | 5/1995 | Birkhahn | |
| 7,351,736 | B2 | 4/2008 | Veech | |
| 11,166,928 | B2* | 11/2021 | Gross | A61K 31/19 |
| 2001/0014696 | A1 | 8/2001 | Veech | |
| 2005/0129783 | A1 | 6/2005 | McCleary et al. | |
| 2009/0197952 | A1 | 8/2009 | Hashim et al. | |
| 2015/0164855 | A1 | 6/2015 | Clarke | |
| 2016/0078782 | A1 | 3/2016 | Meidenbauer et al. | |
| 2018/0177753 | A1 | 6/2018 | Hashim | |
| 2019/0209491 | A1 | 7/2019 | Firger et al. | |

FOREIGN PATENT DOCUMENTS

| AU | 20100207597 A1 | 8/2011 |
| CN | 103877118 A | 6/2014 |
| JP | S61501569 A | 7/1986 |
| JP | H0665458 A | 3/1994 |
| JP | 2001515510 A | 9/2001 |
| WO | 8503872 A1 | 9/1985 |
| WO | 199841200 A1 | 9/1998 |
| WO | 2017011294 A1 | 1/2017 |

OTHER PUBLICATIONS

Krebs, et al., "Metabolism of Acetoacetate in Animal Tissue", Department of Biochemistry and the Medical Research Council Unit for Research in Cell Metabolism, University of Sheffield. 39:408-419, Jul. 4, 1945.
Treiman, David M. et al., "GABAergic Mechanisms in Epilepsy" Epilepsia, 42(Supple. 3):8-12, 2001, 5 pages.
Tsuji, Sadatoshi, "Migraine and epilepsy" Clinical Neurol 54:1003-1005 (2014) ABSTRACT.
Di Lorenzo, C., et al., "Migraine imporvement during short lasting ketogenesis: a proof-of-concept study", European Journal of Neurology 22:170-177 (2015).
Bough, K J et al. "Higher ketogenic diet ratios confer protection from seizures without neurotoxicity." Epilepsy research vol. 38,1 (2000): 15-25. doi:10.1016/s0920-1211(99)00077-7.
Chowdhury, Fahmida A et al. "Investigation of glutamine and GABA levels in patients with idiopathic generalized epilepsy using MEGAPRESS." Journal of magnetic resonance imaging : JMRI vol. 41,3 (2015): 694-9. doi:10.1002/jmri.24611.
Durham, Paul L., "Calcitonin Gene-Related Peptide (CGRP) and Migraine" Headache—vol. 46, Issues1, Jun. 2006, pp. S3-S8.
Farkas, M., Mak, E., Richter, E. et al. EHMTI-0336. Metabolic diet therapy in the prophylactic treatment of migraine headache in adolescents by using ketogenic diet. J Headache Pain 15, G9 (2014). https://doi.org/10.1186/1129-2377-15-S1-G9.

(Continued)

Primary Examiner — Rei Tsang Shiao
(74) Attorney, Agent, or Firm — KDW Firm PLLC

(57) ABSTRACT

The invention relates to a compound for use in a method of treatment or prevention of migraine and/or symptoms thereof. The compound is selected from beta-hydroxybutyric acid (βHB) or a pharmaceutically acceptable salt thereof, acetoacetate (AcAc) or a pharmaceutically acceptable salt thereof, a metabolic precursor of βHB or AcAc 1,3-butanedio and a compound comprising an acetoacetyl- or 3-hydroxybutyrate moiety. The invention further relates to a pharmaceutical composition comprising βHB, AcAc or a pharmaceutically acceptable salt thereof.

22 Claims, 8 Drawing Sheets

(56) References Cited

OTHER PUBLICATIONS

Fraser, D D et al. "Elevated polyunsaturated fatty acids in blood serum obtained from children on the ketogenic diet." Neurology vol. 60,6 (2003): 1026-9. doi:10.1212/01.wnl.0000049974.74242.c6.

Harney, Jacob P et al. "Effects of acute inhibition of fatty acid oxidation on latency to seizure and concentrations of beta hydroxybutyrate in plasma of rats maintained on calorie restriction and/or the ketogenic diet." Epilepsy research vol. 49,3 (2002): 239-46. doi:10.1016/s0920-1211(02)00046-3.

Haut, Sheryl R et al. "Chronic disorders with episodic manifestations: focus on epilepsy and migraine." The Lancet. Neurology vol. 5,2 (2006): 148-157. doi:10.1016/S1474-4422(06)70348-9.

Karsan, Nazia, and Peter J Goadsby. "Calcitonin gene-related peptide and migraine." Current opinion in neurology vol. 28,3 (2015): 250-4. doi:10.1097/WCO.0000000000000191.

Kirby, Ruth., "Calcitonic gene-related peptide and migraine" Nature Clinical Practice—Neurology, Jan. 2006, vol. 2, No. 1, 1 page.

Kossoff, Eric H, and Jong M Rho. "Ketogenic diets: evidence for short- and long-term efficacy." Neurotherapeutics : the journal of the American Society for Experimental NeuroTherapeutics vol. 6,2 (2009): 406-14. doi:10.1016/j.nurt.2009.01.005.

Kossoff, Eric H et al. "Optimal clinical management of children receiving dietary therapies for epilepsy: Updated recommendations of the International Ketogenic Diet Study Group." Epilepsia open vol. 3,2 175-192. May 21, 2018, doi:10.1002/epi4.12225.

Mantegazza, Massimo, and Sandrine Cestèle. "Pathophysiological mechanisms of migraine and epilepsy: Similarities and differences." Neuroscience letters vol. 667 (2018): 92-102. doi:10.1016/j.neulet.2017.11.025.

Musa-Veloso, Kathy et al. "Breath acetone predicts plasma ketone bodies in children with epilepsy on a ketogenic diet." Nutrition (Burbank, Los Angeles County, Calif.) vol. 22,1 (2006): 1-8. doi:10.1016/j.nut.2005.04.008.

Sarlo, Gabrielle L, and Kathleen F Holton. "Brain concentrations of glutamate and GABA in human epilepsy: A review." Seizure vol. 91 (2021): 213-227. doi:10.1016/j.seizure.2021.06.028.

Di Lorenzo, C et al. "Migraine improvement during short lasting ketogenesis: a proof-of-concept study." European journal of neurology vol. 22,1 (2015): 170-7. doi:10.1111/ene.12550.

Kim S. H. et al. Brain & Development, 39:687-692 (2017).

Veech R. L. et al. Energy metabolism and the regulation of metabolic processes in mitochondira: "Liver metabolite content, redox and phosphorylation states in rats fed diets containing 1,3-butanediol and ethanol", pp. 171-183, New York, Academic Press (1972).

Meidenbauer et al. Epilepsy Behav., pp. 48-54 (2014), doi:10.1016/j.yebeh.2014.08.007.

Hashim et al., "Ketone body therapy: from the ketogenic diet to the oral administration of ketone ester" Journal of Lipid Research, vol. 55, 2014, 1818-1826.

Bixel et la., "Generation of Ketone Bodies from Leucine by Cultured Astroglial Cells" J. Neurochem, 1995, 65(6): 2450-61.

Clarke, K., et al., "Kinetics, safety and tolerability of (R)-3-hydroxybutyl (R)-3-hydroxybutyrate in healthy adult subjects", Regulatory Toxicology and Pharmacology, 63(3):401-408 (2012).

Communication pursuant to Article 94(3) EPC for Application No. 17832224.4, dated Sep. 1, 2020, 3 pages.

Desrochers, S., et al.,"Metabolism of (R,S)-1,3-butanediol acetoacetate esters, potential parenteral and enteral nutrients in conscious pigs", American Journal of Physiology-Endocrinology and Metabolism, 268(4):660-667 (1995).

Di Lorenzo, C., et al., "Migraine improvement during short lasting ketogenesis: a proof-of-concept study", European Journal of Neurology 22(1):170-177 (2014).

Kashiwaya, Y., et al., "A Ketone Ester Diet Increases Brain Malonyl-CoA and Uncoupling Proteins 4 and 5 while Decreasing Food Intake in the Normal Wistar Rat*", Journal of Biological Chemistry 285(34):25950-25956 (2010).

Lorenzo et al., European Journal of Neurology, 2015, 12:170-177.

Sherwin, R S. "The effect of ketone bodies and dietary carbohydrate intake on protein metabolism." Acta chirurgica Scandinavica. Supplementum vol. 507 (1981): 30-40.

Szirmai et al., Marmazie (1989), 44(8),570-1 CODEN: PHART; ISSN:0031-7144 (abstract).

Sviatlana, V., et al., "Ketogenic Diet as a Treatment Option for Different CNS Diseases", International Journal of Neurology Research, 2(3-4):285-290 (2016).

Veech, R.L., "Ketone ester effects on metabolism and transcription", Journal of Lipid Research 55:2004-2006 (2014).

Yum et al., "B-Hydroxybutyrate attenuates NMDA-induced spasms in rats with evidence of neuronal stabilization on MR spectroscopy" Epilepsy Res., 2015, 117:125-32.

St-Pierre et al., "Plasma Ketone and Medium Chain Fatty Acid Response in Humans Consuming Different Medium Chain Triglycerides During a Metabolic Study Day" Frontiers in Nutrition | Apr. 16, 2019 | vol. 6 | Article 46.

European Search Report and Written Opinion for EP Application No. 23176972.0, dated Nov. 30, 2023, 8 pages.

Jasper Stefanie et al., "Chronische Schmerzstorung mit somatischen und psychischen Faktoren", psychopraxis, Springer-Verlag, Vienna, vol. 15, No. 5, Jan. 19, 2013, (Jan. 19, 2013), pp. 17-22, XP035310887.

\* cited by examiner

| STUDY PERIOD | SCREENING | BASELINE | INTERVENTION 1 | | WASH-OUT | BASELINE 2 | INTERVENTION 2 | |
|---|---|---|---|---|---|---|---|---|
| VISIT | V1 | V2 | V3 | V4 | | V5 | V6 | V7 |
| TIMEPOINT (IN WEEKS) | -4(+/-2) | 0(+/-2) | 4(+/-1) | 12(+/-1) | | 20(+/-2) | 24(+/-1) | 32(+/-1) |
| ENROLLEMENT | | | | | | | | |
| DEMOGRAPHICS | X | | | | | | | |
| MEDICAL HISTORY | X | | | | | | | |
| PREGNANCY TEST | X | | | | | | | |
| INFORMED CONSENT | X | X | | | | | | |
| INCLUSION/EXCLUSION | X | X | | | | | | |
| RANDOMISATION | | X | | | | | | |
| INTERVENTIONS: | | | | | | | | |
| OBSERVATIONAL RUN-IN | o———o | | | | | o———o | | |
| TREATMENT/PLACEBO 1 | | o———————o | | | | | | |
| WASH-OUT | | | | | o—o | | | |
| TREATMENT/PLACEBO 2 | | | | | | | o———————o | |
| DISPENSING OF STUDY MEDICATION | | X | X | X | | X | X | X |
| COLLECTION OF STUDY MEDICATION | | | X | X | | | X | X |
| ASSESSMENTS: | | | | | | | | |
| ADVERSE EVENTS | | | X | X | | X | X | X |
| VITAL SIGNS [1] | X | X | X | X | | X | X | X |
| PHYSICAL EXAMINATION | X | | | | | | | |
| MIGRAINE DIARY [2] | X | X | X | X | | X | X | X |
| MIDAS & HIT-6 QUESTIONNAIRE [3] | | X | | X | | X | X | X |
| BLOOD KETONE & GLUCOSE LEVEL [4] | | X | X | X | | X | X | X |
| BLOOD DRAW FOR SAFETY ANALYSIS [5] | | X | | X | | X | | X |
| BLOOD DRAW FOR MARKERS OF OXIDATIVE / NITROSATIVE STRESS AND CYTOKINES [7] | | X | X | X | | X | X | X |

FIG. 9

MIGRAINE PREVENTION AND TREATMENT

CROSS-REFERENCE TO RELATED APPLICATIONS

This application is a continuation application of U.S. Ser. No. 16/472,309, filed Jun. 21, 2019, which claims priority to PCT Patent Application Serial No. PCT/EP2017/083880, filed Dec. 20, 2017, entitled "MIGRAINE PREVENTION AND TREATMENT," the contents of which application is expressly incorporated by reference herein.

MIGRAINE PREVENTION AND TREATMENT

The present invention relates to the use of D beta-hydroxybutyric (βHB) acid or a metabolic precursor for the prevention or treatment of migraine or symptoms of migraine.

BACKGROUND

Migraine

Migraine is a complex, genetically heterogeneous, common and debilitating neurological disorder that affects approximately 15% of the world population. With a peak incidence during the most productive years of life, migraine not only causes much suffering, but also inflicts substantial costs on society: approximately € 18.5 billion per year in Europe alone. It is characterized by recurrent moderate to severe, typically throbbing and unilateral headache attacks that last between 4-72 h, which are aggravated by any kind of physical activity and accompanied by either photo-, phono-, or osmophobia, nausea or a combination of these. It is a very heterogeneous disorder, divided into two major subgroups, based on the presence (migraine with aura (MA)) or absence (migraine without aura (MO)) of an aura, a phase of transient and reversible visual, sensory or motor disturbances that typically occurs up to one hour before the attack itself in one third of migraineurs. Migraines are much more than the headache (ictal) phase, as they are typically accompanied by neurological symptoms during a premonitory phase preceding the headache by up to 12 hours and a postdromal phase, which follows the migraine and can last hours or days. To date, the primary migraine pathogenic mechanisms are still largely unknown.

Migraine Therapy

Current migraine treatment options are limited and their mechanisms of action are also not completely understood. While the primary goals of preventative migraine treatment include reducing headache frequency and restoring function, an additional important goal may be the prevention of progression to chronic migraine. None of the prophylactic agents licensed to date (such as beta-blockers, anticonvulsants or antidepressants) are migraine-specific and most are associated with significant—often intolerable—side-effects. Furthermore, their migraine-preventive properties are moderate at most (<25% average reduction in migraine frequency). Hence, there is a huge medical need for developing alternative anti-migraine therapies. The objective of the present invention is to provide novel therapeutic agents for the treatment of migraine, which exhibit improved efficiency and decreased side-effects.

Ketogenic Diet/Endogenous Elevation of KB and Reduction in Glucose

The ketogenic diet (KD) was developed about 100 years ago after the observation that prolonged fasting has anticonvulsive properties. With its high fat, low carbohydrate and protein content it simulates the metabolic effects of starvation. KD has been shown to be an effective alternative when treating refractory epilepsy and albeit its mechanisms are still poorly understood, there is mounting experimental evidence for its broad neuro-protective mechanisms and its potential use in multiple neurological disease states, for example metabolic defects, such as mitochondrial disorders, neurodegenerative disorders, such as Parkinson's Disease and Alzheimer's Disease (AD), trauma and ischemia, narcolepsy and maybe even depression or autism. Nevertheless, clinical evidence on the benefit of ketosis is still mostly confined to refractory epilepsy. Here elevated KB levels achieved via a KD have been shown to be well tolerated for extended periods of time (up to several years). However, a strict KD is unlikely to provide a feasible long-term solution for many patient populations, because it can be difficult to implement in an ambulatory setting and patient adherence may be limited.

Exogenous KB

An alternative means to induce a state of mild to medium nutritional ketosis, irrespective of dietary carbohydrate and protein intake, is the dietary supplementation with exogenous ketogenic substances, such as middle chain triglycerides (MCTs), ketogenic amino acids, βHB or AcAc supplements and more recently keto esters (βHB) and/or AcAc esterified with one another). Dietary supplementation of KB themselves does not require the limitation of carbohydrate and protein, thus increasing the chance of compliance, particularly since carbohydrate diets are common in most cultures.

In comparison to the KD itself, the therapeutic efficacy of KB supplementation is less established to date. Studies in humans using MCTs suggest that those are safe, but in higher therapeutic doses not well tolerated due to strong gastrointestinal upset. Ketone esters have the problem of a very foul taste and while high blood ketone concentrations can be reached, most research has been conducted on gavaged animals. A direct administration of ketogenic acids is potentially dangerous, due to the possibility of acidosis following rapid absorption in the gastrointestinal tract.

Based on the above mentioned state of the art, the objective of the present invention is to provide a new treatment option for migraine by exogenously raising blood KB levels in a safe way with improved palatability and reduced gastrointestinal distress, thereby increasing patient compliance. This objective is attained by the claims of the present specification.

DESCRIPTION OF THE INVENTION

Terms and Definitions

In the context of the present specification, "KB" refers to ketone bodies. Ketone bodies are endogenous metabolites, which are produced by the liver from fatty acids released from adipose tissue in times of starvation, fasting, glucose deprivation or caloric restriction. They can be used as an alternative energy substrate to glucose by most tissues of the body, most notably the brain, which cannot metabolise any other energy substrate apart from glucose and KB. Endogenous KB include beta-hydroxybutyrate (βHB); also known as 3 betahydroxybyturate) and acetoacetate (AcAc). There are some natural exogenous substances that are also ketogenic, such as middle chain triglycerides (MCTs). More recently, other exogenous ketogenic substances have become available, such as βHB mineral salts or keto esters.

In the context of the present specification, the term "ketogenic amino acid" refers to an amino acid that can be degraded to Acetyl-CoA, the precursor of ketone bodies. Leucine and lysine are ketogenic amino acids that are exclusively ketogenic. Isoleucine, phenylalanine, tryptophan and tyrosine are ketogenic amino acids that are also glucogenic.

In the context of the present specification, "βHB" refers to beta-hydroxybutyric acid or beta-hydroxybutyrate, CAS No. 300-85-6.

In the context of the present specification, "βHB" refers to the D enantiomer of βHB.

In the context of the present specification, "AcAc" refers to acetoacetate, CAS No. 541-50-4.

In the context of the present specification, "LL" refers to L-leucine. In the context of the present specification, "LY" refers to L-lysine.

In the context of the present specification, the term "ketogenic diet (KD)" refers to a diet with high fat content, low carbohydrate and medium protein content.

In the context of the present specification, the term "mild to medium nutritional ketosis" refers to a concentration of blood ketone bodies of 0.4-4 mmol/l, which is achieved by a suitable nutrition.

In the context of the present specification, the term "triglyceride" refers to an ester derived from glycerol (CAS No. 56-81-5) and three fatty acids.

In the context of the present specification, the term "fatty acid" refers to an aliphatic monocarboxylic acid comprising a chain of 4 to 28 carbon atoms. The chain can be saturated or unsaturated. The term "free fatty acid" refers to a fatty acid that is not bound to another molecule, e.g. glycerol.

In the context of the present specification, the term "middle chain fatty acid (MCFA)" refers to an aliphatic monocarboxylic acid comprising a chain of 6 to 12 carbon atoms. The chain is saturated.

In the context of the present specification, the term "middle chain triglyceride (MCT)" refers to an ester derived from glycerol (CAS No. 56-81-5) and three MCFA.

In the context of the present specification, "triacetin" refers to 1,2,3-triacetoxypropane, CAS No. 102-76-1.

DETAILED DESCRIPTION OF THE INVENTION

According to a first aspect, the invention provides a compound for use in a method of treatment or prevention of migraine and/or symptoms thereof. The compound is selected from
  a. beta-hydroxybutyric acid (βHB),
  b. acetoacetate (AcAc),
  c. a metabolic precursor of βHB or AcAc,
  d. a compound comprising an acetoacetyl- or 3-hydroxybutyrate moiety.

The metabolic precursor is selected from 1,3-butanediol (CAS No. 107 88 0) and triacetin (CAS No. 102-76-1).

The compound comprising an acetoacetyl- or 3-hydroxybutyrate moiety is described by any one of formulae (Ia) to (Ve)

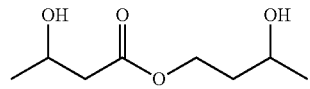
(Ia)

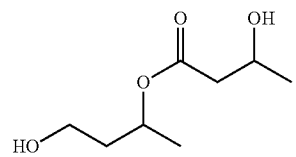
(Ib)

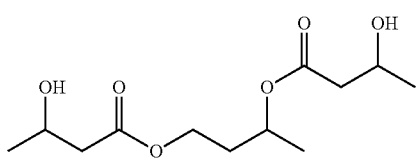
(Ie)

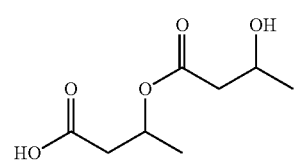
(II)

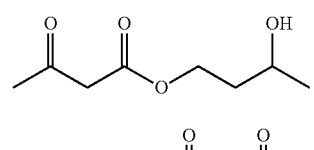
(IIIa)

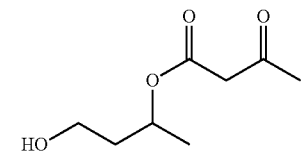
(IIIb)

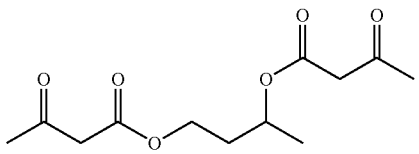
(IIIc)

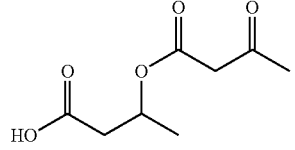
(IV)

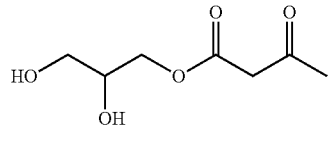
(Va)

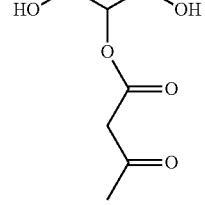
(Vb)

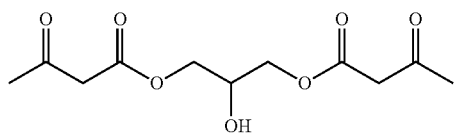
(Vc)

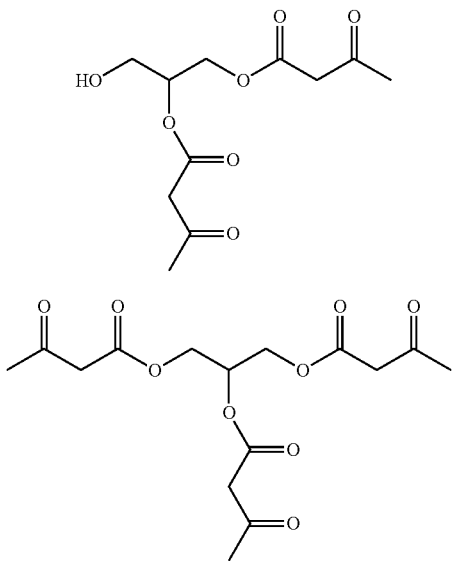

Formula (Ia) specifies 3-hydroxybutyl 3-hydroxybutanoate.

Formula (Ib) specifies (3-hydroxy-1-methyl-propyl) 3-hydroxybutanoate.

Formula (Ie) specifies 3-(3-hydroxybutanoyloxy)butyl 3-hydroxybutanoate.

Formula (II) specifies 3-(3-hydroxybutanoyloxy)butanoic acid.

Formula (IIIa) specifies 3-hydroxybutyl 3-oxobutanoate.

Formula (IIIb) specifies (3-hydroxy-1-methyl-propyl) 3-oxobutanoate.

Formula (IIIe) specifies 3-(3-oxobutanoyloxy)butyl 3-oxobutanoate.

Formula (IV) specifies 3-(3-oxobutanoyloxy)butanoic acid.

Formula (Va) specifies 2,3-dihydroxypropyl 3-oxobutanoate.

Formula (Vb) specifies [2-hydroxy-1-(hydroxymethyl) ethyl]3-oxobutanoate.

Formula (Vc) specifies [2-hydroxy-3-(3-oxobutanoyloxy) propyl]3-oxobutanoate.

Formula (Vd) specifies [3-hydroxy-2-(3-oxobutanoyloxy) propyl]3-oxobutanoate.

Formula (Ve) specifies 2,3-bis(3-oxobutanoyloxy)propyl 3-oxobutanoate.

βHB, AcAc, the metabolic precursor of βHB or AcAc and the compound comprising an acetoacetyl- or 3-hydroxybutyrate moiety can be in the form of a pharmaceutically acceptable salt.

In certain embodiments, the compound is a pharmaceutically acceptable ester of βHB. In certain embodiments, the compound is a pharmaceutically acceptable ester of AcAc.

In certain embodiments, the metabolic precursor of D-βHB is an esterified molecule synthesised using βHB.

In certain embodiments, the compound is an ester of βHB or AcAc with a monohydric, dihydric or trihydric alcohol.

In certain embodiments, the compound is a pharmaceutically acceptable amid of βHB. In certain embodiments, the compound is a pharmaceutically acceptable amid of AcAc.

In certain embodiments, the compound is selected from βHB, AcAc, or pharmaceutically acceptable salt thereof.

In certain embodiments, the compound is selected from βHB, a metabolic precursor of βHB and a compound comprising a 3-hydroxybutyrate moiety and a pharmaceutically acceptable salt of said compounds.

In certain embodiments, the compound is βHB or a pharmaceutically acceptable salt thereof.

In certain embodiments, the compound is D-βHB or a pharmaceutically acceptable salt thereof.

In certain embodiments, the D-βHB is administered in a form which also supplies AcAc.

In certain embodiments, the D-βHB is administered as a metabolic precursor, which when administered to a human or animal body is metabolised, e.g. by liver, to produce D-βHB and AcAc, preferably in a physiological ratio.

A physiologically acceptable salt of the compound according to the invention, in particular in combination with ketogenic amino acids and a mineral mix, offers a way to improve palatability of the compound.

In certain embodiments, the pharmaceutically acceptable salt is selected from a potassium salt, a sodium salt, a calcium salt, a magnesium salt, an arginine salt, a lysine salt, a histidine salt, an ornithine salt, a creatine salt, an agmatine salt, a citrulline salt, a methyl glucamine salt and a carnitine salt, possibly in conjunction with other ketogenic substances. The salt may also be a more complex pharmaceutically acceptable salt.

In certain embodiments, the pharmaceutically acceptable salt is a combination of several of the aforementioned salts. In order to avoid undesirable consequences of some products (e.g. pure sodium salts), it is preferred to use a combination of several mineral salts or a combination of a lysine salt and several mineral salts. By increasing the number of different mineral salts, the total tolerated dose can be increased.

In certain embodiments, the combination of salts comprises a mixture of a lysine salt and a calcium, potassium, magnesium and sodium salt. In certain embodiments, the combination of salts comprises a mixture of a lysine salt and a calcium, potassium, magnesium or sodium salt. In certain embodiments, the combination of salts comprises a lysine salt, a calcium salt, a potassium salt and/or a magnesium salt and/or a sodium salt.

In certain embodiments, the combination of salts is a combination of a lysine salt and a mineral salt. In certain embodiments, the combination of salts is a combination of a lysine, a calcium and a sodium salt.

In certain embodiments, the combination of salts is a combination of a calcium and a sodium salt.

The salts may contain the isomer D-βHB or the racemic DL-βHB.

The compound may be provided alone or in combination with other ketogenic substances.

In certain embodiments, the compound is provided for
(i) decreasing migraine attack frequency;
(ii) decreasing migraine attack severity;
(iii) reducing any of the neurological symptoms associated with migraine, such as phono-, photo-, and/or osmophobia, visual, sensory or motor disturbances, allodynia;
(iv) reducing any of the other features known to accompany, precede or follow a migraine attack, such as fatigue, nausea, cognitive difficulties, tiredness, ravenous hunger or thirst, muscle ache, reduced libido, depression, mania, mood swings;

(v) reversing, retarding or preventing structural or functional nerve cell damage, such as white matter lesions or disturbances in functional connectivity, associated with migraine;

(vi) preventing, retarding or reversing the transition of acute migraine to chronic migraine.

In certain embodiments, the treatment or prevention has the effect of decreasing migraine attack frequency; decreasing migraine attack severity; decreasing the severity of migraine symptoms; preventing disease progression and/or preventing disease chronification.

In certain embodiments, the symptoms of migraine include at least two of the following symptoms: medium to strong predominantly unilateral headache, light, noise and/or smell sensitivity, nausea or sickness, facial pain, sore eyes, balance disturbance, word finding difficulties, other neurological symptoms, such as sensory or motor disturbances, allodynia or any other of the features known to accompany, precede or follow a migraine attack, such as fatigue, nausea, cognitive difficulties, tiredness, ravenous hunger or thirst, reduced libido, depression, mania, mood swings, as well as changes in brain structure and function, such as white matter lesions or disturbances in functional connectivity.

In certain embodiments, the compound is to be administered before symptoms of a migraine attack, in particular those recited in the previous paragraph, occur.

In certain embodiments, the daily dose to be administered is 0.05 g/kg to 1 g/kg body weight (=3.5-70 g/70 kg). In certain embodiments, the daily dose to be administered is 0.1 g/kg to 0.7 g/kg body weight (=7-49 g/70 kg). In certain embodiments, the daily dose to be administered is 0.2 g/kg 0.4 g/kg body weight (=14-28 g/70 kg).

In certain embodiments, the daily dose to be administered is 3.5 g to 70 g. In certain embodiments, the daily dose to be administered is κ g to 50 g. In certain embodiments, the daily dose to be administered is 10 g to 40 g. In certain embodiments, the daily dose to be administered is 10 g to 40 g.

In certain embodiments, the daily dose to be administered is 10 g. In certain embodiments, the daily dose to be administered is 20 g.

The inventors have examined the effect of various ketogenic substances, such as LL, LY, racemic and D-βHB on blood KB levels (pharmokokinetic), tolerability and migraine attack frequency. MCTs were not used due to known problems with tolerability and palatability.

LL, but not LY was shown to lead to a very small increase (up to 0.35 mmol/I) in blood βHB over approximately 4 hours. The ketogenic amino acids were not well tolerated, it was impossible for the patients to consume 26 g of amino acids per day. The bitter taste further contributed to the problem.

In comparison, βHB was well tolerated and had a strong effect on blood KB levels.

Surprisingly, the D-βHB isomer led to a more than threefold elevation in blood βHB levels (up to 1.94 mmol/I) as compared to the racemic version. Levels remained elevated for over 4 hours. In addition, there was no concomitant drop in blood glucose, as observed with the racemic mix. Participants reported the taste was improved (less foul) and fewer gastrointestinal side-effects were observed, even with 2 months consumption. Efficacy data suggest that surprisingly as little as 10 g of D-βHB daily might match the efficacy of 40 g of the racemic mix, with an average of 68.5% reduction in migraine days with 10 g of D-βHB compared to 72% reduction with 40 g racemic βHB.

Exogenous KB in quantities much lower than produced by the liver during a KD or fasting (20 g instead of around 150 g) were found to have a migraine preventive effect. Racemic βHB salts led to an increase in βHB blood levels approximately double of LL (up to 0.62 mmol/I), but the half-life was very short, with levels dropping back to baseline after 2 hours. In addition, a substantial drop in blood glucose levels was observed. Tolerability and palatability of the racemic βHB was problematic, in particular gastrointestinal upset and nausea. 20 g daily were found to reduce average migraine day frequency by 51%. This reduction ranged from 25-80%. Despite fairly good efficacy only 2 out of 5 patients continued to take the racemic βHB salts. An increased dose of 40 g racemic βHB lead to a further reduction of 72% in migraine days. Nevertheless, this increased dose exacerbated the side-effects.

In certain embodiments, the daily dose is divided into one to six doses. In certain embodiments, the daily dose is divided into two doses. In certain embodiments, the daily dose is divided into three doses.

In certain embodiments, the daily dose is to be administered over a time period of at least one month. In certain embodiments, the daily dose is to be administered over a time period of at least 6 months. In certain embodiments, the daily dose is to be administered over a time period of at least one year. In certain embodiments, the daily dose is to be administered over a time period of 2 years.

In certain embodiments, the administration of said compound to a subject causes elevation of blood ketone body (KB) levels to 0.3 mM to 6 mM. In certain embodiments, the administration of said compound to a subject causes elevation of blood ketone body (KB) levels to 0.4 mM to 4 mM. In certain embodiments, the administration of said compound to a subject causes elevation of blood ketone body (KB) levels to 1 mM to 4 mM.

According to a second aspect of the invention, a pharmaceutical composition is provided for use in the treatment or prevention of migraine and/or symptoms thereof comprising the compound according to the first aspect of the invention. The pharmaceutical composition can be a medicament or a nutritional aid.

In certain embodiments of this aspect of the invention, the pharmaceutical composition is a formulation or dosage form. In certain embodiments, the dosage form is a powder, tablet, gas or a solution.

In order to mask the potentially bitter taste of lysine, the pharmaceutical composition may comprise *stevia* and/or other artificial sweeteners (saccharin, acesulfame, sucralose), menthol, citrus, berry or other flavours.

In certain embodiments of this aspect of the invention, the pharmaceutical composition is a combination medicament further comprising an amino acid selected from the group comprising leucine, lysine, isoleucine, tryptophan, tyrosine and phenylalanine. The components of the combination medicament can be administered simultaneously or one after another.

In certain embodiments of this aspect of the invention, the content of the compound according to the first aspect of the invention in the pharmaceutical composition is at least 25% (w/w). In certain embodiments of this aspect of the invention, the content of the compound according to the first aspect of the invention in the pharmaceutical composition is at least 35% (w/w). In certain embodiments of this aspect of the invention, the content of the compound according to the first aspect of the invention in the pharmaceutical composition is 50% to 100% (w/w).

In certain embodiments of this aspect of the invention, the pharmaceutical composition is to be administered to a subject diagnosed with migraine suffering from 1 to 31 migraine days per months.

In certain embodiments of this aspect of the invention, the pharmaceutical composition is to be administered before symptoms of a migraine attack occur.

In certain embodiments of this aspect of the invention, the daily dose to be administered of said compound comprised in the pharmaceutical composition is 0.05 g/kg to 1 g/kg body weight, preferably 0.1 g/kg to 0.7 g/kg body weight, more preferably 0.2 g/kg to 0.4 g/kg body weight (depending on disease severity).

In certain embodiments of this aspect of the invention, the daily dose is divided into one to six doses, particularly into two or three doses.

In certain embodiments of this aspect of the invention, the daily dose is to be administered over a time period of at least one month, preferably at least 6 months, most preferably over 2 years.

In certain embodiments of this aspect of the invention, the pharmaceutical composition is formulated for oral administration. In certain embodiments of this aspect of the invention, the pharmaceutical composition is formulated for parenteral administration. In certain embodiments of this aspect of the invention, the pharmaceutical composition is formulated for any other form of conventional administration.

In certain embodiments of this aspect of the invention, the pharmaceutical composition is formulated as a powder for oral administration. The powder is dissolved in water prior to consumption.

In certain embodiments of this aspect of the invention, the pharmaceutical composition is a drink.

In certain embodiments of this aspect of the invention, the administration of said pharmaceutical composition to a subject causes elevation of blood ketone body (KB) levels to 0.3 mM to 6 mM, particularly to 0.4 mM to 4 mM, more particularly to 1 mM to 4 mM.

The inventors' results suggest that between 5 g to 70 g of KB, particularly 5 g to 40 g of βHB, more particularly 10 g to 20 g of βHB per patient per day are required to achieve this. The necessary elevation for migraine freedom will depend on disease severity (i.e. number of migraine days per months).

According to another aspect of the invention, a method of treatment or prevention of migraine and/or symptoms thereof is provided, comprising administration of the compound according to the first aspect of the invention or the pharmaceutical composition according to the second aspect of the invention to a subject in need thereof.

In certain embodiments, the subject in need is suffering from 1 to 31 migraine days per month.

In certain embodiments, the subject in need shows manifestation of at least two of the following symptoms of migraine: medium to strong predominantly unilateral headache, light, noise and/or smell sensitivity, nausea or sickness, facial pain, sore eyes, balance disturbance, word finding difficulties, other neurological symptoms, such as sensory or motor disturbances, allodynia or any other of the features known to accompany, precede or follow a migraine attack, such as fatigue, nausea, cognitive difficulties, tiredness, ravenous hunger or thirst, reduced libido, depression, mania, mood swings, as well as changes in brain structure and function, such as white matter lesions or disturbances in functional connectivity.

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

BRIEF DESCRIPTION OF THE FIGURES

FIG. 2A: Depicted are βHB blood levels inmmol/l (y-axis) before (Baseline=0 h) and after (0.5, 1, 2, 3 h, 4 h) 10 g of βHB consumption in 5 migraine patients. βHB was given in powdered sodium-calcium-salt form dissolved in water on an empty stomach. Blood βHB concentrations were measured using a portable point-of-care blood ketone meter (Precision Xtra®) and matching test stripes. Error bars depict the standard error of the means (SEM). FIG. 2B: Blood glucose levels in mmol/l (y-axis) before (Baseline value=0 h) and after the consumption of 10 g βHB ante cibum in 5 migraine patients. The rise in blood glucose from 1 h onwards corresponds to the intake of a mixed food breakfast (food intake indicated by the arrow) one hour after consumption of βHB, which was given to prevent potential hypoglycemia. Blood glucose concentrations were measured using a portable point-of-care blood ketone meter (Precision Xtra®) and matching test stripes. Error bars depict the standard error of the means (SEM).

FIG. 5A: Depicted are βHB blood levels in mmol/l (y-axis) before (Baseline=0 h) and after (0.5, 1, 2, 3 h, 4 h) 10 g of βHB consumption. DβHB was given in powdered mixed mineral and lysine-salt form dissolved in water on an empty stomach. Blood βHB concentrations were measured using a portable point-of-care blood ketone meter (Precision Xtra®) and matching test stripes. Error bars depict the standard error of the means (SEM). FIG. 5B: Blood glucose levels in mmol/l (y-axis) before (Baseline value=0 h) and after the consumption of 10 g βHB ante cibum. Blood glucose concentrations were measured using a portable point-of-care blood ketone meter (Precision Xtra®) and matching test stripes. Error bars depict the standard error of the means (SEM).

Figure 1:
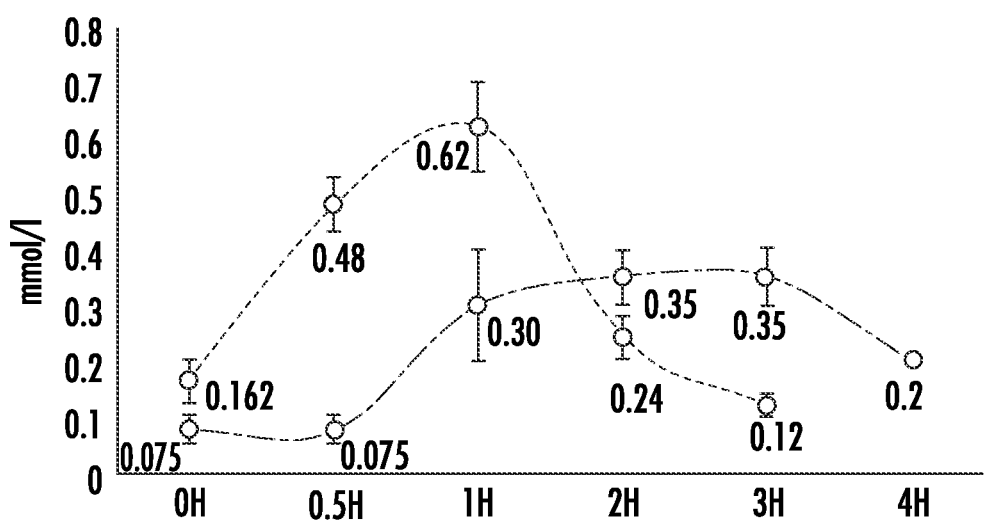
FIG. 1 shows the pharmacokinetics of 13 g L-leucine (LL) ante cibum in 2 migraine patients (grey) compared to 10 g βHB (black). Depicted are βHB blood levels in mmol/l (y-axis) before (baseline=0 h) and after (0.5, 1, 2, 3, 4 h) 13 g of LL (grey) and 10 g βHB consumption (black) respectively in 2 migraine patients. Substances were given in powdered form, dissolved in water on an empty stomach. Blood βHB concentrations were measured using a portable point-of-care blood ketone meter (Precision Xtra®) and matching test stripes. Error bars depict the standard error of the means (SEM).

Average number of migraine days (y-axis) at baseline (white) in 2 high-frequency migraineurs (17 and 10 migraine days/month) and the reduction in average monthly migraine days after 8 weeks of intervention with 10 g racemic βHB (grey) versus 10 g D-βHB (black). Blood βHB concentrations were measured using a portable point-of-care blood ketone meter (Precision Xtra®) and matching test stripes.

FIG. 9 is a table showing a detailed study schedule for a double-blind, randomized, placebo-controlled, safety, tolerability and efficacy trial with one active intervention (betaHb) and one placebo group. (Key: [1]Blood pressure, heart rate, weight, height; [2]Pen and paper headache diary;[3]Migraine Disability Questionnaire and Headache Impact Test, German versions, standard questionnaires for assessing the extent of migraine related disability; [4]Blood beta-hydroxybutyrate and glucose levels, measured with a portable ketone meter (precision xtra by Abbot); [5]Routine laboratory (renal and liver function tests, electrolytes, full blood count, C reactive protein, serum cholesterol, triglycerides, serum proteins, albumin, glucose, Hba1c, insulin, cortisol, lactate, TSH, FT4 and FT3); [6]Blood draw (1×EDTA, 1×PAXgene) at each time point for genetic profiling and gene expression analysis using microarrays; 7 Blood draw at each time point for oxidative and nitrosative stress markers (malondialdehydes (MDA), carbonylated proteins, nitrite, nitrotyrosine) and serum cytokine measurements (including but not limited to: IF Nγ, IL-1β, IL-2, IL-4, IL-5, IL-6, IL-10, MCP-1, TNFα&β, TGF-β1).

EXAMPLES

1. Pilot Experiments

Patients diagnosed with medium-high frequency or chronic migraine according to International Headache Society Classification version 3 by an experienced neurologist were included. They were excluded if they had any significant other neurological, psychiatric or medical disorder. A minimum average of 6 migraine days/month was required during the last 3 months. Ten migraine patients (age range: 25-61 years, 1 male, attack frequency range: 6-24 migraine days/months) were included in the pilot study and randomly assigned to four conditions: 1) L-leucine (LL), 2) L-lysine (LY), 3) racemic βHB, 4) D-βHB.

1.1. Preliminary Pharmacokinetics on 13 g L-Leucine and 13 g L-Lysine in 4 Migraine Patients L-leucine (LL) and L-lysine (LY) are the two completely ketogenic amino acids. Via various steps, unused ketogenic amino acids (i.e. leucine or lysine) are metabolised into KB. While this is commonly known, to the best of our knowledge no data exists on the extent and time frame of such ketogenic amino acids to raise blood βHB levels. For the pharmacokinetics, four migraine patients were instructed to ingest either 13 g LL or 13 g LY on an empty stomach. Blood βHB and glucose concentrations were measured using a portable point-of-care blood ketone meter (Precision Xtra®) and matching test stripes at 5 points in time: 1) Baseline (directly before consumption), 2) 0.5 h after consumption, 3) 1 h after consumption, 4) 2 h after consumption, 5) 3 h after consumption and 6) 4 h after consumption. 13 g roughly correspond to the same number of particles (mmol) as 10 g βHB. Highest average concentrations of βHB were found after 2 and 3 h (mean=0.35 mmol/l; SEM=0.05) and remained levels to remain elevated for over 4 hours (see FIG. 1). With LY no blood βHB elevations could be measured at all.

Preliminary results of the L-leucine (3 patients) and L-lysine (2 patients) intervention:

Monthly migraine attack frequency was summarized over the last 3 months and the average was used for baseline comparison. Patients were either instructed to take 26 g LL or 26 g LY in two daily doses (one hour before breakfast and one hour before dinner, respectively) for the duration of 4 weeks. They were instructed to refrain from any other changes in medication or food habits for the duration of that period. The primary outcome measure was changes in days with migraines from baseline. Days with migraine were recorded using a mobile app (myheadache.ch) or a pen and paper diary and averaged across participants.

Adverse events occurred in all patients from the beginning of the trial, such as diarrhoea or nausea when 26 g of LL or LY daily were consumed (13 g twice a day) and the bitter taste of the powder was intolerable. One patient in the LL group already dropped out during the pharmacokinetic part of the trial. The dose had to be drastically reduced and long-term use of a high dose of those ketogenic amino acids is unlikely to be feasible due to palatability and feasibility issues. In addition, the dose reduction made the data incomparable and the very slight or non-measurable increases in blood βHB levels would have made the results hard to interpret with regards to mechanisms of action.

1.2. Preliminary Pharmacokinetics on 10 g Racemic βHB in 5 Migraine Patients

Figure 2A:
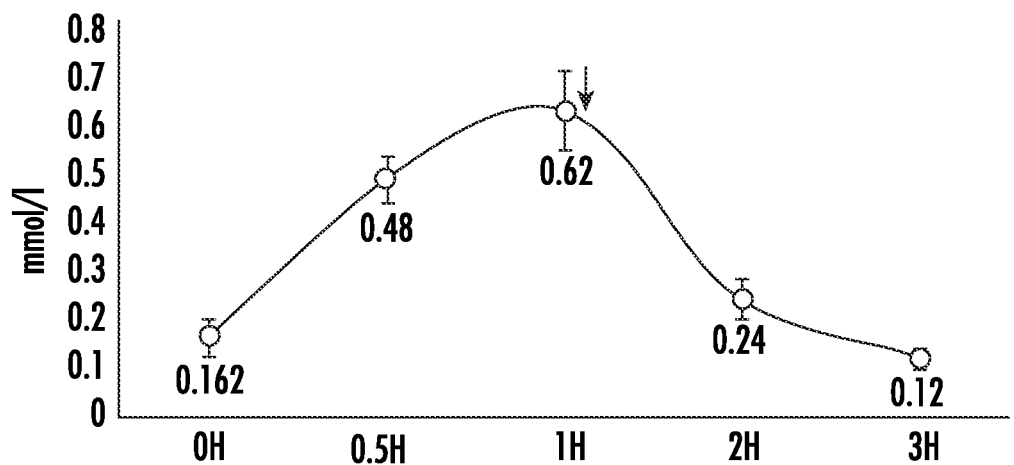
FIG. 2(A) and FIG. 2(B) show the pharmacokinetics of 10 g racemic beta-hydroxybutyrate (BHB) ante cibumon 5 migraine patients and its effect on glucose levels.

For determining pharmacokinetics, the patients were given 10 g racemic beta-hydroxybutyrate (βHB) orally dissolved in water in 3 different conditions: (1) post cibum (after meal) (2) ante cibum (before meal) (3) 1 hour before meal. Blood βHB and glucose concentrations were measured using a portable point-of-care blood ketone meter (Precision Xtra®) and matching test stripes at 5 points in time: 1) Baseline (directly before consumption), 2) 0.5 h after consumption, 3) 1 h after consumption, 4) 2 h after consumption, 4)3 h after consumption and 6) 4 h after consumption. Greatest elevations of βHB blood levels were demonstrated when βHB was consumed fasted (results depicted in FIG. 2A). Highest average concentrations of βHB were found after approximately 1 h (mean=0.62 mmol/l; SEM=0.08), which is approximately double the amount of LL. The levels dropped to near baseline after 2 hours.

Figure 2B:
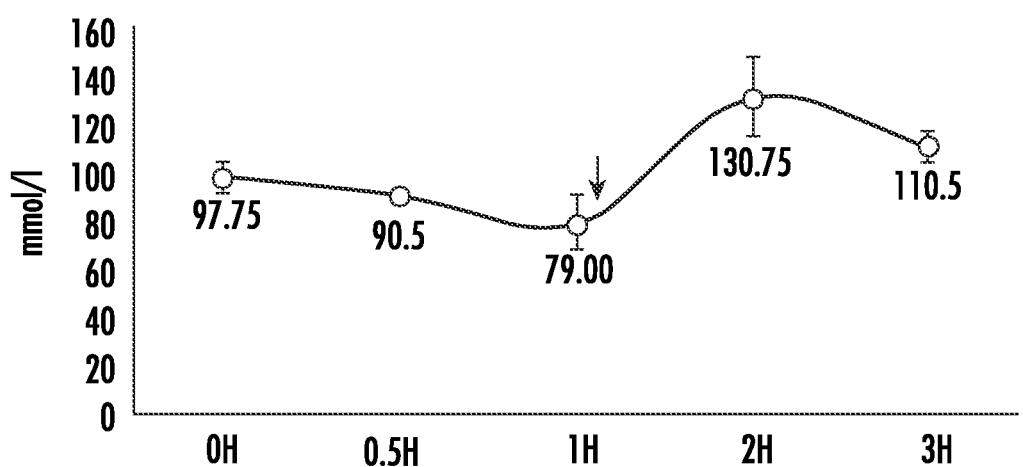

Glucose levels were measured at the same time as βHB, in order to examine the effect of βHB on glucose levels. FIG. 2B shows that the increase of βHB blood levels after 0.5 and 1 h is accompanied by a concomitant substantial drop in blood glucose levels. In order to prevent hypoglycaemia, a mixed meal was provided and measurements continued.

1.3. Preliminary Efficacy of 20 g Racemic βHB in 5 Patients (Open-Label Intervention on 5 Patients)

Monthly migraine attack frequency was summarized over the last 3 months and the average was used for baseline comparison. Patients were either instructed to take 20 g βHB, 26 g LL or 26 g LY in two daily doses (one hour before breakfast and one hour before dinner, respectively) for the duration of 4 weeks. They were instructed to refrain from any other changes in medication or food habits for the duration of that period. The primary outcome measure was changes in days with migraines from baseline. Days with migraine were recorded using a mobile app (myheadache.ch) or a pen and paper diary and averaged across participants.

Intolerable adverse events occurred in one patient, who reported severe nausea and vertigo after consumption and dropped out 8 days after intervention onset. The other 4 patients also experienced gastrointestinal upset, which got a bit better the powder was taken with or after dinner. The palatability remained an issue, with a foul taste being reported. In sum, tolerability and palatability of the racemic βHB was problematic, in particular gastrointestinal upset and nausea, which might be further exacerbated by the accompanying drop in blood glucose levels after consumption.

Figure 3:
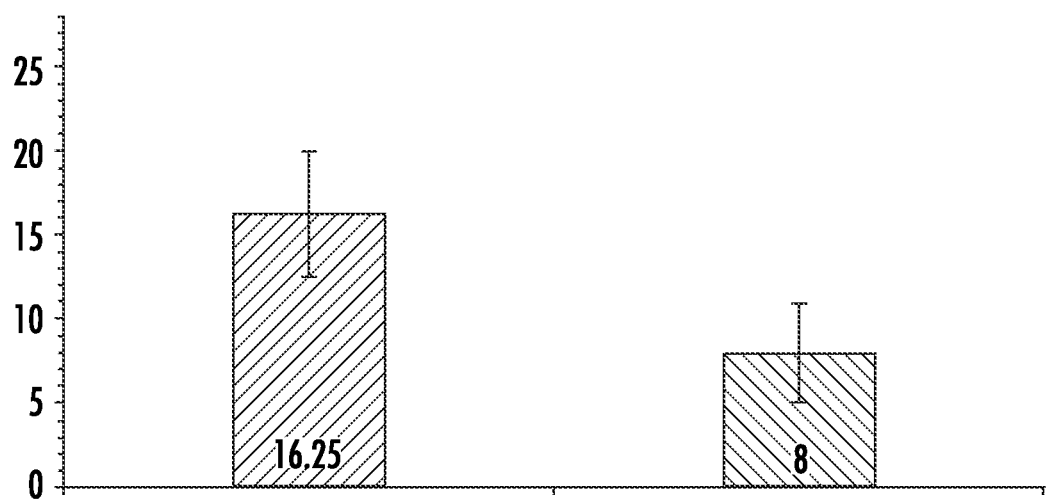
FIG. 3 shows the effect of 20 g βHB daily on days with migraine. Average number of migraine days (y-axis) at baseline (black) in a group of 4 medium-high frequency migraineurs (6-22 migraine days/month) and the reduction in migraine days after 4 weeks of intervention with 20 g βHB daily (grey). Similar to the average, the median at baseline is 18 migraine days and at 7 migraine days after the intervention. Blood βHB concentrations were measured using a portable point-of-care blood ketone meter (Precision Xtra®) and matching test stripes. Error bars depict the standard error of the means (SEM).

There was an average reduction of 51% in migraine days compared to baseline (mean baseline=16.25 days, SEM=3.71; mean after βHB=8 days, SEM=2.92; see FIG. 3). This reduction ranged from 25-80%. Despite fairly good efficacy only 2 out of 5 patients continued to take the racemic βHB salts, after the 4 weeks were completed.

Figure 4A:
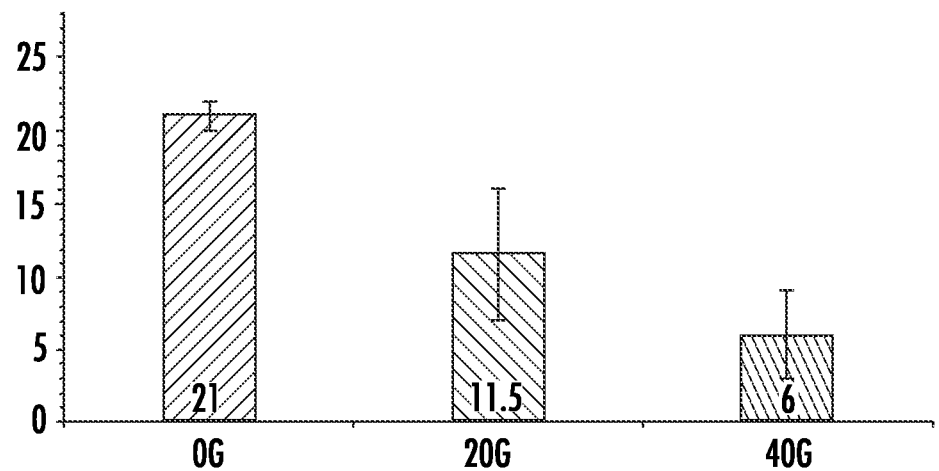
FIG. 4A shows the dose dependent effect of 20 g βHB or 40 g βHB on days with migraine. Average number of migraine days (y-axis) at baseline (black) in 2 chronic migraineurs (20 or 22 migraine days/month) and the reduction in migraine days after 4 weeks of intervention with 20 g βHB (grey) and 40 g βHB (white dotted). Blood βHB concentrations were measured using a portable point-of-care blood ketone meter (Precision Xtra®) and matching test stripes. Error bars depict the standard error of the means (SEM).
Figure 4B:
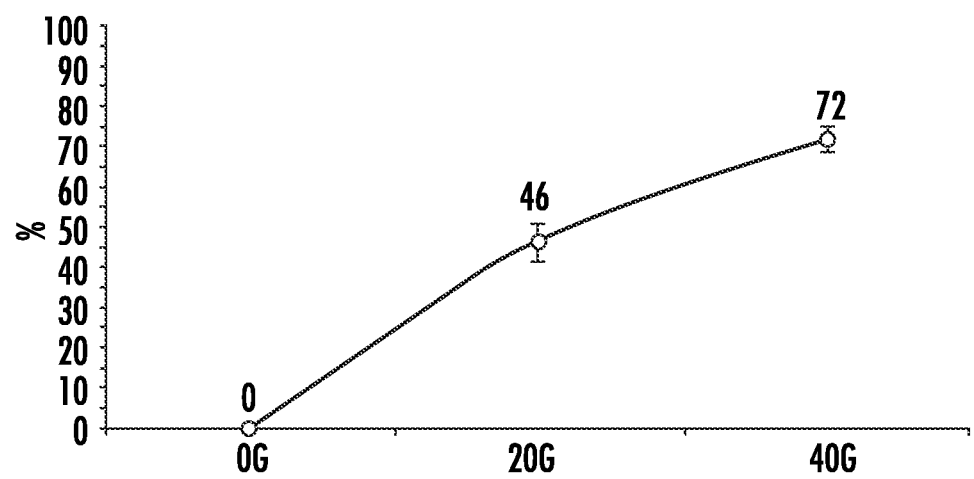
FIG. 4B shows the dose response curve to 0, 20 and 40 g βHB daily (percent reduction in migraine days from baseline). Percent in reduction in migraine days from baseline (y-axis) after 4 weeks of 0 g βHB daily (0 g), after 4 weeks of 20 g βHB daily (20 g) and after 4 weeks of 40 g βHB daily (40 g) in 2 chronic migraineurs (20 or 22 migraine days/month). Blood βHB concentrations were measured using a portable point-of-care blood ketone meter (Precision Xtra®) and matching test stripes. Error bars depict the standard error of the means (SEM).

Dose Response Data (20 g Versus 40 g βpHB):

Those two chronic migraineurs (20 or 22 migraine days/month) where instructed to take 20 g racemic βHB daily for 4 weeks and after a 1 week washout period double the dose to 40 g βHB for the following 4 weeks. Migraine days were recorded for the duration of the intervention and patients were instructed to refrain from any other life-style or medication changes. The mean baseline attack frequency was 21 migraine days (SEM=1) and dropped to 11.5 days after 4 weeks of 20 g βHB daily and 6 days after 4 weeks of 40 g βHB daily (see FIG. 4A). This preventive effect is roughly proportional to the increase in dose, with 20 g βHB leading to 46% reduction in migraine days from baseline (SEM=18.86) and 40 g βHB to a 72% reduction (SEM=12.95; see FIG. 4B). This preliminary observation suggests that the migraine preventive effect of βHB is likely to be dose dependent. Nevertheless, the increased dose also increased side-effects further in both patients and 40 g of foul tasting powder per day also seemed difficult to consume in the longer term.

1.4. Preliminary Pharmacokinetics on 10 g D-βHB in 5 Participants

Figure 7:
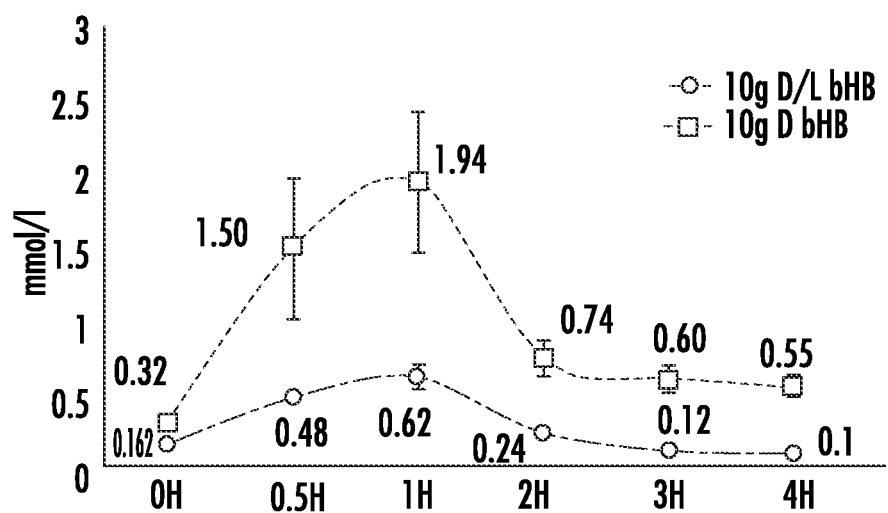
FIG. 7 shows the comparison of pharmacokinetics of 10 g racemic DL-beta-hydroxybutyrate (βHB (black) and 10 g D-βHB (grey) ante cibum on 5 participants at baseline. Depicted are βHB blood levels in mmol/l (y-axis) before (Baseline=0 h) and after (0.5, 1, 2, 3, 4 h) 10 g of βHB consumption. Racemic βHB was given in powdered sodium-calcium-salt form, D-βHB was given in powdered mixed mineral and lysine-salt form, both dissolved in water on an empty stomach. Blood βHB concentrations were measured using a portable point-of-care blood ketone meter (Precision Xtra®) and matching test stripes. Error bars depict the standard error of the means (SEM).

Participants were given 10 g D-beta-hydroxybutyrate βHB orally dissolved in water in a fasted state. Blood βHB and glucose concentrations were measured using a portable point-of-care blood ketone meter (Precision Xtra®) and matching test stripes at 5 points in time: 1) Baseline (directly before consumption), 2) 0.5 h after consumption, 3) 1 h after consumption, 4) 2 h after consumption, 5) 3 h after consumption and 6) 4 h after consumption (see FIG. 5A). As with racemic βHB, highest average concentrations of βHB were found after approximately 1 h (mean=1.94 mmol/l; SEM=0.48). However, to the inventors' surprise the peak levels were more than triple the amount achieved with the racemic βHB (see FIG. 7).

Figure 5A:
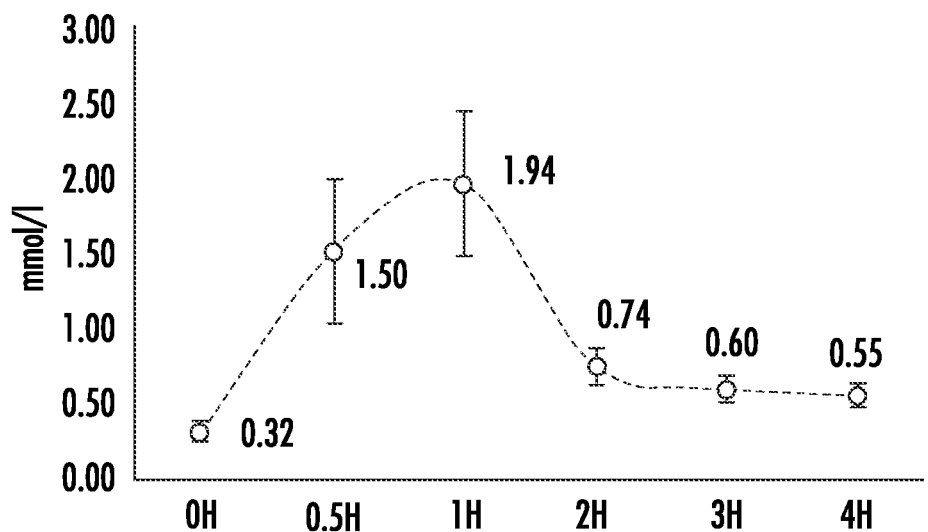
FIG. 5(A) and FIG. 5(B) show the pharmacokinetics of 10 g D-beta-hydroxybutyrate (βHB ante cibum on 5 participants and its effect on glucose levels.

In addition, the βHB levels remained elevated even after 4 hours (FIG. 5A).

Figure 5B:
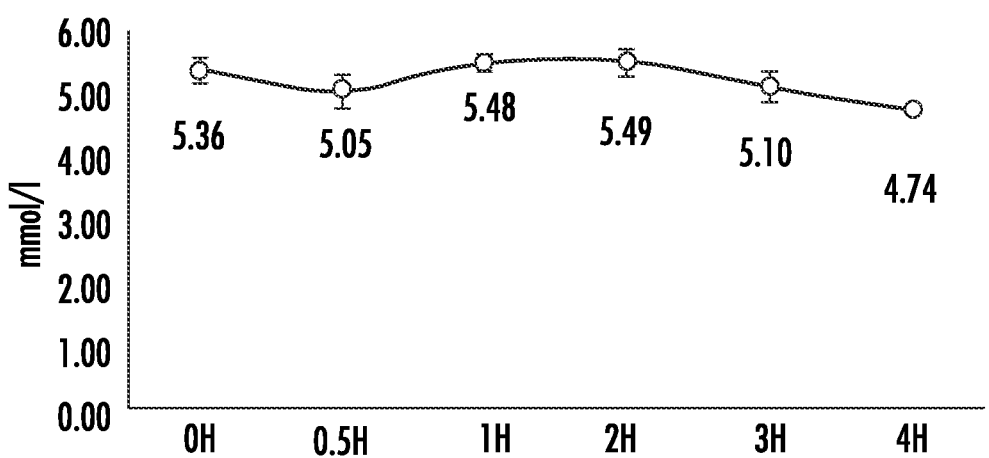
Figure 6:
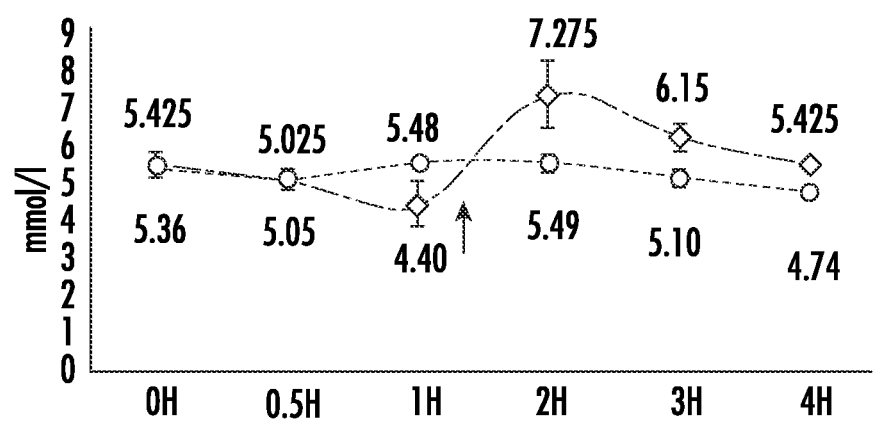
FIG. 6 shows the comparison of the effect of a one-time dose of either 10 g racemic beta-hydroxybutyrate βHB or 10 g D-βHB on blood glucose levels (in mmol/l; y-axis) before (Baseline value=0 h) and after the consumption of either 10 g racemic βHB (black) or D-βHB (grey). The rise in blood glucose from 1 h onwards in the case of the racemic βHB corresponds to the intake of a mixed food breakfast (food intake indicated by the arrow) one hour after consumption of βHB, which was given to prevent potential hypoglycemia. Blood glucose concentrations were measured using a portable point-of-care blood ketone meter (Precision Xtra®) and matching test stripes. Error bars depict the standard error of the means (SEM).

Glucose levels were measured at the same time as βHB, in order to examine the effect of D-βHB on glucose levels. To the inventors' surprise, the high average elevation of βHB blood levels to almost 2 mmol/l is not accompanied by a concomitant change in blood glucose levels, which seem to stay completely stable throughout the 4 hours (see FIG. 5B). This is in contrast to the drop in blood glucose patients experienced with racemic βHB (see FIG. 6); it did not seem to occur when consuming the same amount of D-βHB.

1.5. Preliminary Efficacy of 10 g Racemic βHB Versus 10 g D-βHB on 2 Patients (Open-Label Intervention)

Monthly migraine attack frequency was summarized over the last 3 months and the average was used for baseline comparison. Patients were instructed to take 10 g racemic βHB for the duration of 8 weeks, followed by one week wash-out period and then 8 weeks of 10 g D-βHB daily. They were instructed to refrain from any other changes in medication or food habits for the duration of that period. The primary outcome measure was changes in days with migraines from baseline. Days with migraine were recorded using a mobile app (myheadache.ch) or a pen and paper diary and averaged across participants.

Figure 8:
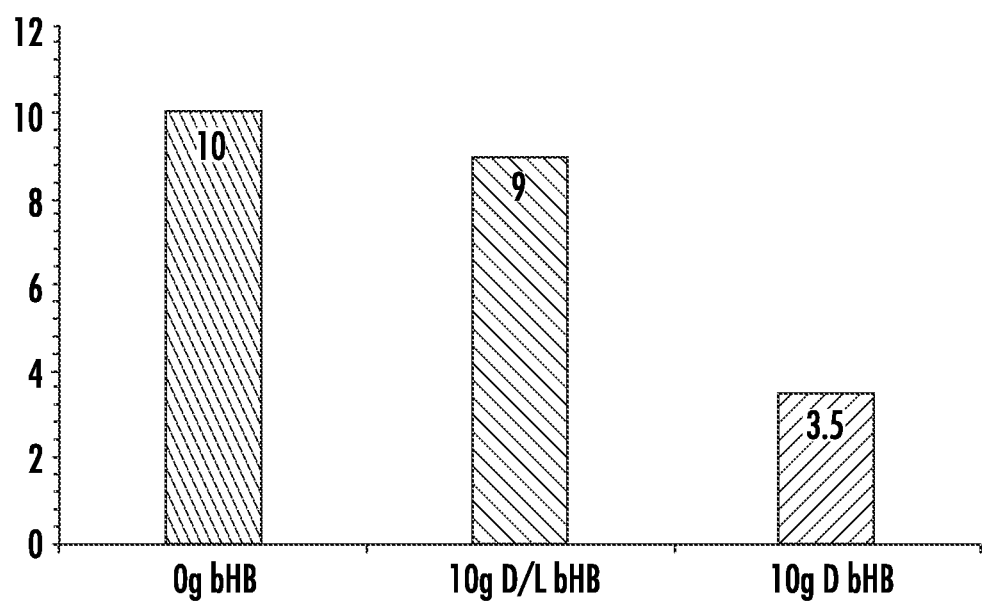
FIG. 8 shows the effect of 10 g racemic βHB versus 10 g D-βHB daily on migraine frequency.

During the 8 weeks of 10 g racemic βHB, an average reduction of 18.5% in migraine days compared to baseline (mean baseline=13.5 days, SEM=2.86; mean after βHB=11 days, SEM=1.15; see FIG. 8) was observed. During the 8 weeks of 10 g D-βHB, an average reduction of 68.5% in migraine days compared to baseline (mean baseline=13.5 days, SEM=2.86; mean after βHB=4.25 days, SEM=0.43; see FIG. 8) was observed. This reduction in migraine days is comparable to the effect observed with 40 g racemic βHB (both approximately 70% reduction in days with migraine).

Palatability and side-effect profile were much improved with the DβHB and the reduced dose. No side-effects were reported at the given dose. And both patients are continuing to take D-βHB on a daily basis.

These very preliminary findings suggest that surprisingly DβHB not only seems to be able to raise blood βHB levels much higher than other ketogenic substances in the human, but also leads to a pronounced reduction in migraine frequency (up to 70%) with only a fraction of the dose the human body produced during a KD (10 g versus approx. 150 g). In addition, it seems to be much better tolerated and more palatable than other ketogenic substances and does not seem to lead to a potentially unwanted drop in blood glucose levels. This finding suggests that D-βHB might not only act as a metabolite in the migraine patient, but also a signalling molecule, which positively impacts migraine relevant pathophysiological mechanisms.

2. Clinical Trial

Clinical trial description: Safety, tolerability and efficacy of exogenous ketone bodies for preventive treatment of migraine: A cross-over randomised, placebo-controlled, double-blind study.

2.1. Clinical Trial Synopsis

| | |
|---|---|
| Principal/Coordinating Investigator | Dirk Fischer, MD, Professor of Neurology<br>Consultant Neurologist<br>Division of Neuropediatrics<br>University of Basel Children's Hospital<br>Spitalstrasse 33<br>CH-4056 Basel, Switzerland<br>Phone: +41 61 704 2918<br>Fax: +41 61 704 1277<br>E-mail: Dirk.Fischer@ukbb.ch |
| Title of clinical trial | Long title: Safety, tolerability and efficacy of exogenous ketone bodies for preventive treatment of migraine: A cross-over randomised, placebo-controlled, double-blind study<br>Short title: Exogenous ketone bodies in migraine prevention (MigraKet) |
| Clinical trial type and phase | A cross-over double blind randomized placebo-controlled phase 2 safety and efficacy trial |
| Objective(s) | To test if exogenous beta-hydroxybutyrate treatment, compared to placebo, reduces migraine frequency in episodic migraineurs (5-14 migraine days/month) by 25% at least (using change in days with migraine as assessed by a headache diary as primary clinical endpoint). |
| Intervention(s) | Experimental intervention: 18 g beta-hydroxybutyrate in mineral salt form per day (taken orally)<br>Control intervention: Matched placebo<br>Duration of intervention per patient: 2 × 12 weeks<br>Duration of wash-out period per patient: 8 weeks |
| Key inclusion and exclusion criteria | Key inclusion criteria: Diagnosis of episodic migraine (5-14 migraine days/month, 18-65 years old, stable preventive treatment for >3 months<br>Key exclusion criteria: Any significant neurological, psychiatric or other medical condition, Botox within 6 months of study onset, anti-month, current participation in other migraine trial |
| Endpoint(s) | Primary endpoint: Change from baseline in days with migraine during last 4 weeks of intervention<br>Secondary endpoint(s): Change in migraine Disability Assessment, change in migraine intensity (VAS 0-10), change in days with medication use, change in headache days of any severity<br>Exploratory endpoint(s): Change in markers of markers of oxidative stress, gene expression changes, genetic profile, peak KB and blood glucose level change from baseline |
| Sample size | Number of patients to be assessed for eligibility: 54<br>Number of patients to be allocated to the trial: 45<br>Number of patients to be analysed: 32 |
| Statistical analysis | Efficacy: ANCOVA of primary endpoint, intention-to-treat set of patients<br>Description of the primary efficacy analysis and population: ANCOVA, intention-to-treat set<br>Safety: ANCOVA, intention-to-treat set<br>Secondary endpoints: ANCOVA, intention-to-treat set |
| Trial duration | First patient in to last patient out (months): 27<br>Recruitment period (months): 21<br>Duration of the entire trial (months): 36 |
| Participating centres | Single Centre, University Children's Hospital Basel, Switzerland |
| Key words | Migraine, prevention, double blind randomised placebo-controlled clinical trial, exogenous KB, genetics |

2.2. Study Medicament

In order raise blood ketone levels exogenously, the inventors propose the use of D-βHB, or a metabolic precursor thereof, alone or in combination with other ketogenic substances, in the manufacture of a medicament or nutritional aid for the treatment of prevention or migraine or symptoms thereof.

For feasibility reasons and mineral load, patients in the phase 2 trial described below are dosed with 18 g βHB in mineral salt form. In the following the study medicament will be referred to as *verum*.

2.3. Study Design

The study is a double-blind, randomised, placebo-controlled, safety, tolerability and efficacy trial with one active intervention βHB and one placebo group. 45 medium- to high-frequency migraineurs (5-14 migraine days/months) aged between 18 and 65 years are included. Participants are required to keep a detailed headache diary (www.myheadache.ch), for the entire duration of the study.

The study period will begin with a 4 week run-in period, during which there is no investigation al treatment (see FIG. 1). The purpose of the run-in period will be observation when the subjects will receive the study medicament or matched placebo (three times a day). The first intervention period will be followed by an 4 week wash-out period and a second 4 week run-in period during which there will be no further intervention. This will be followed by the second intervention period, when the participants will "cross-over", i.e. received the alternative treatment of the first intervention (if they received *verum* the first 12 weeks, they will receive placebo the second 12 weeks or the other way round).

2.4. Targeted Outcomes

2.4.1. Primary Efficacy Outcome Measure.

The primary objective is to show in moderate- to high-frequency episodic migraineurs the superiority of the *verum* to placebo with regard to the reduction in migraine days per 4 weeks from baseline to the last 4 weeks of intervention.

A detailed pen and paper headache diary (similar to www.myheadache.ch) is used to assess the reduction in monthly migraine frequency (i.e. the primary outcome). Reduction of days with migraine (assessed with headache diaries) is the standard primary efficacy outcome measure in RCTs on migraine prevention. The headache diary is available as IOS and android app and is easy to use. Migraine related features such as attack begin, length of attack (in hours), severity of attack (0-10), medication taken (amount and dose), associated symptoms and potential trigger factors are recorded.

2.4.2. Secondary Efficacy Outcome Measures

Secondary objectives are to assess the therapeutic efficacy of externally induced mild ketosis by the *verum* regarding the following secondary endpoints:

Rate of treatment responders, defined as >50% reduction in migraine days.

Change in number of headache days of any severity from baseline (meeting ICHD-3 criteria) during the last 4 weeks of intervention.

Change in number of headache days of any severity from baseline (meeting ICHD-3 criteria) during the last 4 weeks of follow-up.

Change in consumption of acute migraine medication from baseline (analgesics or triptans)—measured in days with acute headache medication use—during the last 4 weeks of intervention.

Change in average migraine intensity from baseline—assessed with a VAS from O-10 for each migraine episode—during the last 4 weeks of the intervention period.

Change in disability from baseline—assessed with the Migraine Disability Assessment (MIDAS), indicating the number of days with migraine-related disability (0-270)—and the Headache Impact Test 6 (HIT-6) to the last 4 weeks of the intervention period.

The secondary outcomes will be measured using the headache diary (myheadache.ch) and the questionnaires, which will be provided as paper copy during the baseline visit, the visit after the 12 weeks interventions and after the wash-out period respectively.

2.4.3. Exploratory Analyses

Exploratory objectives are to assess the potential mechanisms of action of externally induced mild ketosis by D-βHB supplementation regarding markers of oxidative stress and genetic analyses:

Serum concentration changes from baseline of oxidative and nitrosative stress markers (malondialdehyde (MDA), carbonylated proteins, nitrate, nitrite, nitrotyrosine) during the last 4 weeks of intervention, examined with ELISA and mass spectroscopy.

Genetic profile (SNPs) of all patients involved in the study and correlation of the genetic markers with primary and secondary outcomes.

Gene expression changes before and after intervention using expression microarrays with a special focus on mitochondrial related genes citrate synthase, cytochrome C oxidase subunit 1, succinate dehydrogenase subunit A).

Correlation of gene expression changes with the genetic profile of the patients (eQTL analysis) in combination with primary and secondary outcomes as possible covariates.

A further exploratory objective is to examine the change of peak BK levels and glucose levels from baseline to the last 4 weeks of the intervention period. Blood KB and glucose levels will be measured using a portable point-of-care blood ketone meter (Precision Xtra® and matching test stripes) once a week in the morning, 30 min and 60 min after consumption of the study medicament.

2.4.4. Tolerability and Safety Outcome Measures:

Safety and tolerability will be determined by:

Comparison of treatment-emergent adverse events (any event regardless of potential causality with the drug) between placebo and active treatment.

Comparison of treatment-related adverse events (such as gastrointestinal upset) as imputed by the principal investigator between placebo and active treatment.

Any significant changes on routine laboratory and vital signs (see below) compared to baseline and/or placebo group.

Routine laboratory (renal and liver function tests, electrolytes, full blood count, C reactive protein, serum cholesterol, triglycerides, serum proteins, albumin, glucose, Hba1c) will be examined at visit 2, 3 and 4 to determine safety of the treatment. The vital parameters (blood pressure, heart rate, weight, height) will be measured at every visit.

2.5. Selection of Trial Subjects

2.5.1. Recruitment

Recruitment Strategies

Patients are informed about the study during the doctor's consultation at the Department of Neurology, University Hospital Basel by their neurologist (e.g. Dr. Bernhard Decard). More flyers are displayed in local pharmacies, local neurologists, the neurological department of the Bruderholzspital (Kantonsspital Baselland) and the Headache Clinic of Bad Zurzach (by Prof. Sandor). In addition, patients previously contacted for a migraine-sport intervention study at the USB (EKNZ-Number 194/13) are contacted again, if they previously agreed and met inclusion criteria for the current study. About 300 research interested patients previously contacted for this study agreed to be contacted for future studies on migraine prevention. Moreover, there are flyers publicly displayed in the waiting room of the neurology and general medicine department, as well as the University Library. An announcement similar to the flyer is posted on the webpages of the University of Basel "Marktplatz" dedicated to research studies (https://markt.unibas.ch/nc/inserate/kategorie/job-angebot-studien/) as well as the USB Website respectively (https://www.unispital.basel.ch/lehre-forschung/studieninserate/).

Feasibility of Recruitment

Trial readiness is high in medium- to high-frequency migraine patients as current therapeutic options are very limited and associated with often intolerable side-effects. Migraine is a prevalent disorder and the inventors already have a contingent of 300 patients willing to take part in research on new forms of migraine inventions. Additionally, the co-applicant has access to a big patient pool through his Headache Clinic and together with the neurology department of the USB approximately 100 patients meet inclusion criteria. The inventors are not anticipating any problems with the recruitment of 50 eligible patients.

2.5.2. Inclusion and Exclusion Criteria

Inclusion Criteria: The subject
1. Is between the ages of 18 and 65 years.
2. Has been previously diagnosed with migraine (with or without aura) in accordance with the ICHD-3 Beta Classification criteria.
3. Experience between 5 and 14 migraine days per month (over the last 3 months) with at least 2 of the migraines lasting more than 4 hours.
4. Has age of onset of migraine less than 50 years old.
5. Agrees to refrain from initiating or changing the type, dosage or frequency of any prophylactic medications (exclusive of medications taken for acute relief of migraine symptoms) as well as dietary supplements (such as 010, riboflavin etc.) against migraine and for indications other than migraine that in the opinion of the clinician may interfere with the study objectives (e.g. antidepressant, anticonvulsants, beta blockers, etc.) for the duration of the study.
6. Has not changed type, dosage or frequency of any prophylactic medications (exclusive of medications taken for acute relief of migraine symptoms) as well as dietary supplements (such as 010, riboflavin etc.) against migraine and for indications other than migraine that in the opinion of the clinician may interfere with the study objectives (e.g. antidepressant, anticonvulsants, beta blockers, etc.) for at least 3 months prior to study onset.
7. Agrees to use the ketogenic powder or placebo as intended, follow all of the requirements of the study including follow-up visit requirements, record required study data in the subject dairy and other self-assessment questionnaires and is okay with drawing blood samples.
8. Is able to provide written Informed Consent.

Exclusion Criteria: The subject
1. Has a concomitant medical condition that will require oral or injectable steroids during the study.
2. Has a history of any significant neurological, psychiatric or other medical condition that in the opinion of the investigator may confound the study assessments
3. Is currently treated for a thyroid disease or has a history thereof.
4. Has a cardiovascular disease (hypertension in particular) or a history thereof.
5. Has a known history of suspected secondary headache.
6. Currently takes simple analgesics or non-steroidal anti-inflammatory drugs (NSAIDs) or triptans greater than 10 days per month for headaches or other body pain.
7. Currently takes prescription opioids.
8. Has previous diagnosis of medication overuse headache (MoH), which has reverted to episodic migraine within the last 6 months.
9. Meets the ICHD-3 Beta Classification criteria for chronic migraine (>15 headache days per month).
10. Has failed an adequate trial (two months or greater) of at least 3 classes of a drug therapy for the prophylaxis of migraine.
11. Has had surgery for migraine prevention.
12. Has received Botox injections within the last 6 months.
13. Is pregnant or plans to become pregnant during the study period, or of childbearing years and is unwilling to use an accepted form of birth control.
14. Is participating in any other therapeutic clinical investigation or has participated in a clinical trial in the preceding 30 days.
15. Belongs to a vulnerable population or has any condition such that his or her ability to provide informed consent, comply with the follow-up requirements, or provide self-assessments is compromised (e.g. homeless, developmentally disabled and prisoner).
16. Is thinking to start, change or stop a hormone-based contraception.

2.6. Statistics

The primary objective is to show in moderate- to high-frequency episodic migraineurs the superiority of the ketogenic supplement to placebo with regard to the reduction in migraine days per 4 weeks from baseline to the last 4 weeks of intervention. The primary endpoint, number of migraine days in the last four weeks of treatment, will be measured twice for each patient, once after the placebo treatment period and once after the *verum* treatment period. The number of migraine days in the four weeks before start of treatment will be assessed for both treatment periods, thus there will be two baseline values than will be used as covariates. This has the aim of correcting for any potential seasonal variation in baseline migraine frequency or carry-over effects The primary analysis will be performed using a linear, mixed effects regression model.

The primary model will include the primary endpoint— number of migraine days in the last four weeks of treatment—as response variable, the respective baseline value as covariate, treatment (*verum* vs placebo) and period (first vs. second) as main effects, the two interaction terms "treatment×period" and "treatment×baseline value", and patient as random effect. A significant interaction term between treatment and period would indicate a carry-over effect. Since it is not known how strong the primary end-point correlates with the baseline value, it is not known whether including the base-lines as covariates in the model is sensible. Therefore, the above described primary model will be compared to models without interaction term "treatment× baseline value" and without both interaction term "treatment×baseline value" and baseline value as covariate by means of Akaike's Information Criterion (AIC).

The primary analysis will be done on the ITT set. Missing values will be imputed as described in section 11.5.

Subgroup analyses: The following a priori defined subgroups will be investigated: sex (male/female), migraine with aura (yes/no), baseline frequency of migraine days (medium=5-9 days/4 weeks; high=10-14 days/4 weeks For each subgroup, the main effect of the subgroup and the interaction term "subgroup×treatment" will be added to the above described statistical model. In case of a trend (p<0.10) for an interaction effect—indicating a difference in the treatment effect between the subgroups-, separate models will be fit for each subgroup.

Sensitivity analysis: The main analysis, without subgroup analyses, will be repeated on the PP set. Potential deviations from the results of the ITT analysis will be described in detail.

Secondary endpoints will be analysed as described for the primary endpoint with the corresponding baseline measure as covariate, if available. A further exploratory objective is to examine the correlation of BK levels with the number of migraine days per 4 weeks from baseline to the last 4 weeks of the follow-up period. The time courses of both variables will be graphically displayed and inspected. Further, the cross-correlation will be calculated.

Statistical considerations for the other exploratory objectives (gene expression changes, changes in markers of oxidative stress and potential genetic basis underlying treatment response) are outlined below.

The statistical analysis will be performed using R (http://www.r-project.org/).

The invention claimed is:

1. A method of treatment or prevention of migraine and/or symptoms thereof in a patient in need thereof, said method comprising administering to the patient a compound which is a metabolic precursor of βHB selected from the group consisting of
   (i) a pharmaceutically acceptable ester of beta-hydroxybutyrate (βHB),
   (ii) a pharmaceutically acceptable ester of acetoacetate (AcAc),
   (iii) a compound comprising an acetoacetyl- or 3-hydroxybutyrate moiety,
   (iv) a keto ester,
   (v) a middle chain triglyceride (MCT), and
   (vi) a pharmaceutically acceptable salt of any one of (i) to (v).

2. The method of claim 1, wherein said compound is a metabolic precursor of D-beta-hydroxybutyrate (D-βHB).

3. The method of claim 1, wherein said compound is a metabolic precursor, which when administered to a human or animal body is metabolised to produce D-βHB and AcAc.

4. The method of claim 1, wherein said compound is an ester formed by the union of βHB or AcAc with a monohydric, dihydric or trihydric alcohol.

5. The method of claim 1, wherein said compound is an ester formed by the union of βHB with βHB, βHB with AcAc, or AcAC with AcAc.

6. The method of claim 1, wherein said compound is a pharmaceutically acceptable ester of D-βHB.

7. The method of claim 1, wherein said compound is
(i) any one of: D-beta-hydroxybutyrate-D-1,3-butanediol, (3R)-hydroxybutyl-(3R)-hydroxybutyrate, acetoacetyl-1,3-butanediol, acetoacetyl-R-3-hydroxybutyrate, or acetoacetylglycerol;
(ii) any one of:
    3-hydroxybutyl 3-hydroxybutanoate,
    (3-hydroxy-1-methyl-propyl) 3-hydroxybutanoate,
    3-(3-hydroxybutanoyloxy)butyl 3-hydroxybutanoate,
    3-(3-hydroxybutanoyloxy)butanoic acid,
    3-hydroxybutyl 3-oxobutanoate,
    3-hydroxy-1-methyl-propyl) 3-oxobutanoate,
    3-(3-oxobutanoyloxy)butyl 3-oxobutanoate,
    3-(3-oxobutanoyloxy)butanoic acid,
    2,3-dihydroxypropyl 3-oxobutanoate,
    [2-hydroxy-1-(hydroxymethyl)ethyl]3-oxobutanoate,
    [2-hydroxy-3-(3-oxobutanoyloxy)propyl]3-oxobutanoate,
    [3-hydroxy-2-(3-oxobutanoyloxy)propyl]3-oxobutanoate, or
    2,3-bis(3-oxobutanoyloxy)propyl 3-oxobutanoate; or
(iii) any one of the formulae:

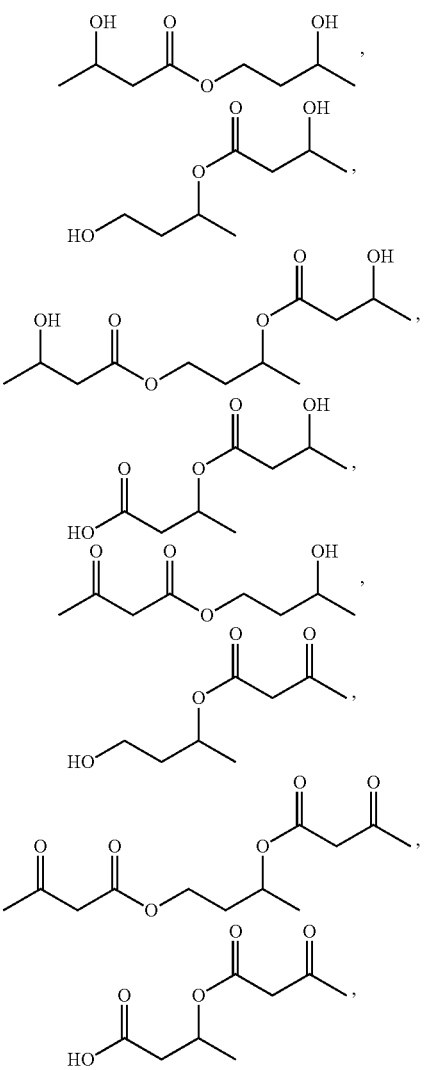

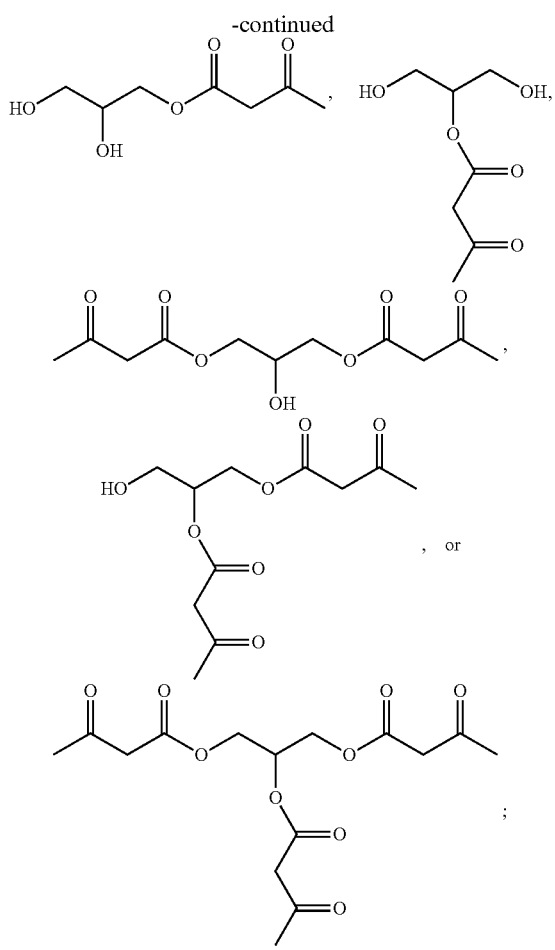

or a pharmaceutically acceptable salt thereof.

8. The method of claim 1, wherein said pharmaceutically acceptable salt is selected from the group consisting of a potassium salt, a sodium salt, a calcium salt, a magnesium salt, an arginine salt, a lysine salt, a histidine salt, an ornithine salt, a creatine salt, an agmatine salt, a citrulline salt, a methyl glucamine salt, a carnitine salt, and any combination of said salts.

9. The method of claim 1, wherein said treatment or prevention includes decreasing migraine attack frequency; decreasing migraine attack severity;
decreasing the severity of migraine symptoms; preventing disease progression; or
preventing disease chronification.

10. The method of claim 1, wherein said symptoms of migraine include at least two symptoms selected from the group consisting of: medium to strong predominantly unilateral headache; light, noise and/or smell sensitivity; nausea or sickness; facial pain; sore eyes; balance disturbance; word finding difficulties; sensory or motor disturbances; allodynia; and at least one symptom known to accompany, precede or follow a migraine attack selected from fatigue, nausea, cognitive difficulties, tiredness, ravenous hunger or thirst, reduced libido, depression, mania, and mood swings.

11. The method of claim 1, wherein the daily dose to be administered is 0.05 g/kg to 1 g/kg body weight.

12. The method of claim 11, wherein said daily dose is divided into one to six doses.

13. The method of claim 11, wherein said daily dose is administered to the patient for at least one month.

14. The method of claim 1, wherein the administration of said compound to the patient causes elevation of blood ketone body (KB) levels to 0.3 mM to 6 mM.

15. A method of treatment or prevention of migraine and/or symptoms thereof in a patient in need thereof comprising administering to the patient a pharmaceutical composition comprising the compound according to claim 1.

16. The method of claim 15, wherein said pharmaceutical composition is a combination medicament further comprising an amino acid selected from the group consisting of leucine, lysine, isoleucine, tryptophan, tyrosine and phenylalanine.

17. The method of claim 15, wherein the pharmaceutical composition is formulated for oral administration.

18. The method according to claim 15, wherein the pharmaceutical composition is formulated as a powder for oral administration or as a drink.

19. The method according to claim 15, wherein the content of the compound in the pharmaceutical composition is at least 25% (w/w).

20. The method according to claim 15, wherein the content of the compound in the pharmaceutical composition is 50% to 100% (w/w).

21. The method according to claim 15, wherein said pharmaceutical composition further comprises *stevia* and/or another artificial sweetener, or menthol, or a flavour.

22. The method according to claim 15, wherein said pharmaceutical composition is administered to a subject diagnosed with migraine suffering from 1 to 31 migraine days per months.

* * * * *